(12) United States Patent
Masunishi et al.

(10) Patent No.: US 10,206,654 B2
(45) Date of Patent: *Feb. 19, 2019

(54) PRESSURE SENSOR, MICROPHONE, ULTRASONIC SENSOR, BLOOD PRESSURE SENSOR, AND TOUCH PANEL

(71) Applicant: Kabushiki Kaisha Toshiba, Minato-ku (JP)

(72) Inventors: Kei Masunishi, Kawasaki (JP); Akiko Yuzawa, Kawasaki (JP); Yoshihiko Fuji, Kawasaki (JP); Michiko Hara, Yokohama (JP); Yoshihiro Higashi, Komatsu (JP); Kazuaki Okamoto, Yokohama (JP); Kenji Otsu, Yokohama (JP)

(73) Assignee: Kabushiki Kaisha Toshiba, Minato-ku (JP)

( * ) Notice: Subject to any disclaimer, the term of this patent is extended or adjusted under 35 U.S.C. 154(b) by 72 days.

This patent is subject to a terminal disclaimer.

(21) Appl. No.: 15/254,377

(22) Filed: Sep. 1, 2016

(65) Prior Publication Data

US 2017/0067787 A1    Mar. 9, 2017

(30) Foreign Application Priority Data

Sep. 9, 2015    (JP) .................................. 2015-177999

(51) Int. Cl.
*A61B 8/00* (2006.01)
*A61B 5/021* (2006.01)
(Continued)

(52) U.S. Cl.
CPC ............ *A61B 8/44* (2013.01); *A61B 5/02141* (2013.01); *G01L 9/0042* (2013.01);
(Continued)

(58) Field of Classification Search
CPC .................................. A61B 8/44; G01L 9/0042
(Continued)

(56) References Cited

U.S. PATENT DOCUMENTS

| 9,618,411 B2 * | 4/2017 | Yuasa ...................... G01L 9/16 |
| 2003/0079549 A1 * | 5/2003 | Lokhorst ................. G01L 1/205 |
| | | 73/754 |

(Continued)

FOREIGN PATENT DOCUMENTS

| CN | 101264859 A | 9/2008 |
| JP | 2013-205403 | 10/2013 |
| TW | 201323845 A1 | 6/2013 |
| TW | 201514818 A | 4/2015 |
| TW | 201521682 A | 6/2015 |

OTHER PUBLICATIONS

Patrick R. Scheeper et al. "The Design, Fabrication, and Testing of Corrugated Silicon Nitride Diaphragms", Journal of Microelectromechanical Systems, vol. 3, No. 1, 1994, 7 pages.

*Primary Examiner* — Lisa Caputo
*Assistant Examiner* — Jamel Williams
(74) *Attorney, Agent, or Firm* — Oblon, McClelland, Maier & Neustadt, L.L.P.

(57) ABSTRACT

A pressure sensor of an embodiment includes a support portion, a transformable membrane part and a sensor portion. The membrane part includes an end portion supported by the support portion, and a first area and a second area. The first area is positioned between a center of the membrane part and the end portion and has a first rigidity. The second area is positioned between the first area and the end portion, and has a second rigidity lower than the first rigidity. The sensor portion is provided at the first area and includes a first magnetic layer, a second magnetic layer and a first intermediate layer provided between the first magnetic layer and the second magnetic layer. An end-side distance between the (Continued)

first area and the end portion is shorter than a center-side distance between the second area and the center of the membrane part.

20 Claims, 11 Drawing Sheets

(51) Int. Cl.
G06F 3/041 (2006.01)
G01L 9/00 (2006.01)
H04R 15/00 (2006.01)

(52) U.S. Cl.
CPC .......... *G01L 9/0054* (2013.01); *G06F 3/0414* (2013.01); *H04R 15/00* (2013.01); *A61B 2562/0247* (2013.01); *H04R 2201/003* (2013.01); *H04R 2410/00* (2013.01)

(58) Field of Classification Search
USPC .................................................. 73/862.632
See application file for complete search history.

(56) References Cited

U.S. PATENT DOCUMENTS

| | | | |
|---|---|---|---|
| 2007/0186666 A1* | 8/2007 | Ruehrig | G01L 1/12 73/779 |
| 2008/0160659 A1 | 7/2008 | Craddock et al. | |
| 2012/0055257 A1* | 3/2012 | Shaw-Klein | H01L 41/081 73/780 |
| 2013/0170669 A1* | 7/2013 | Fukuzawa | G01L 9/0042 381/115 |
| 2013/0255393 A1* | 10/2013 | Fukuzawa | G01L 1/12 73/779 |
| 2015/0088008 A1 | 3/2015 | Fuji et al. | |
| 2015/0338300 A1* | 11/2015 | Masunishi | G01L 9/16 73/725 |
| 2016/0003697 A1* | 1/2016 | Okamoto | G01L 9/0041 73/862.632 |
| 2016/0009545 A1* | 1/2016 | Fuji | G01L 9/0042 257/419 |
| 2016/0202800 A1 | 7/2016 | Itaya et al. | |

* cited by examiner

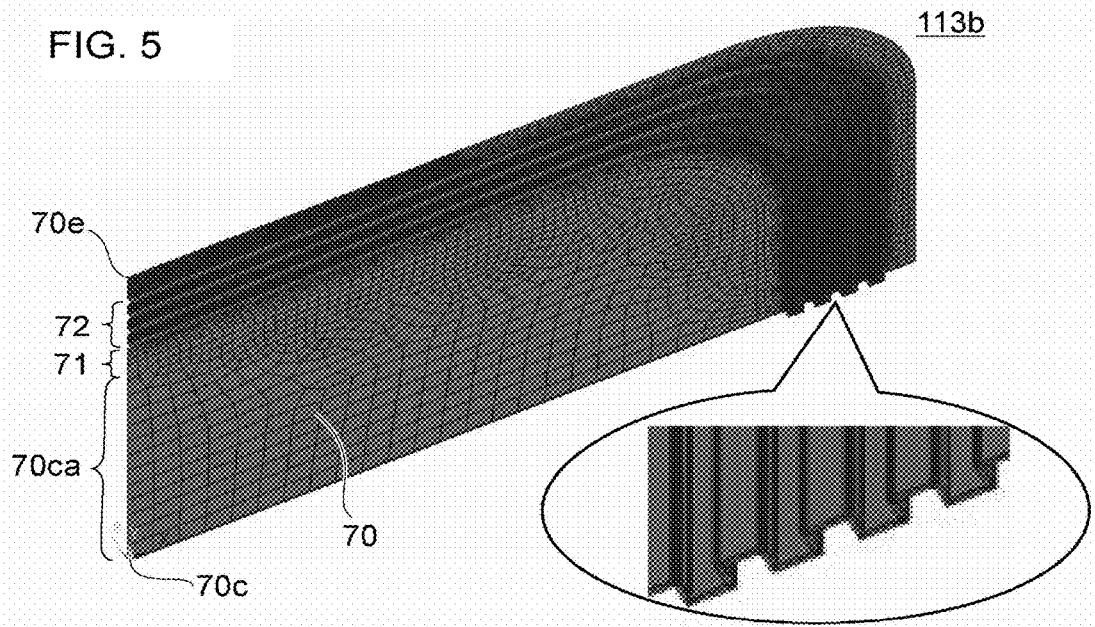

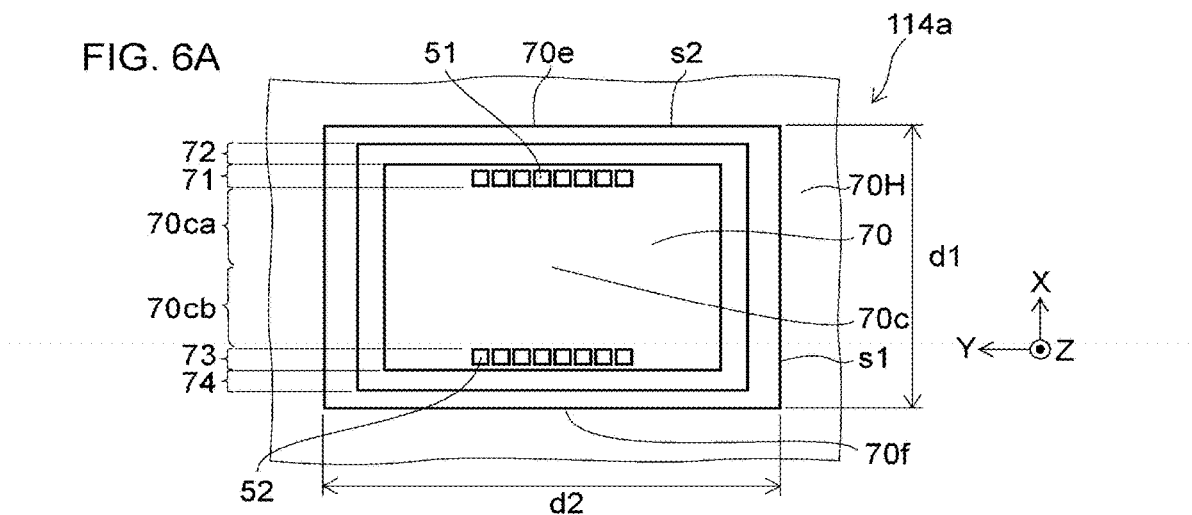
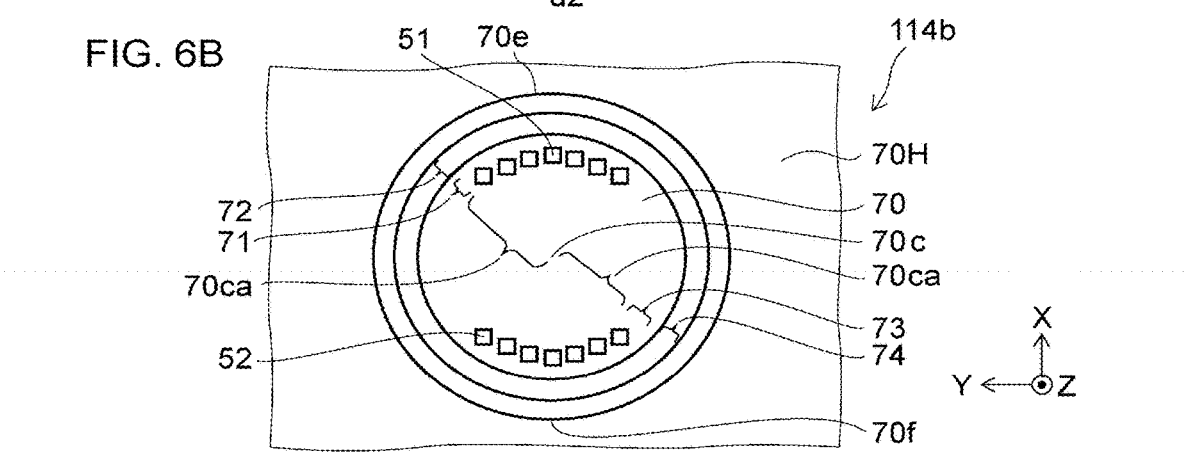
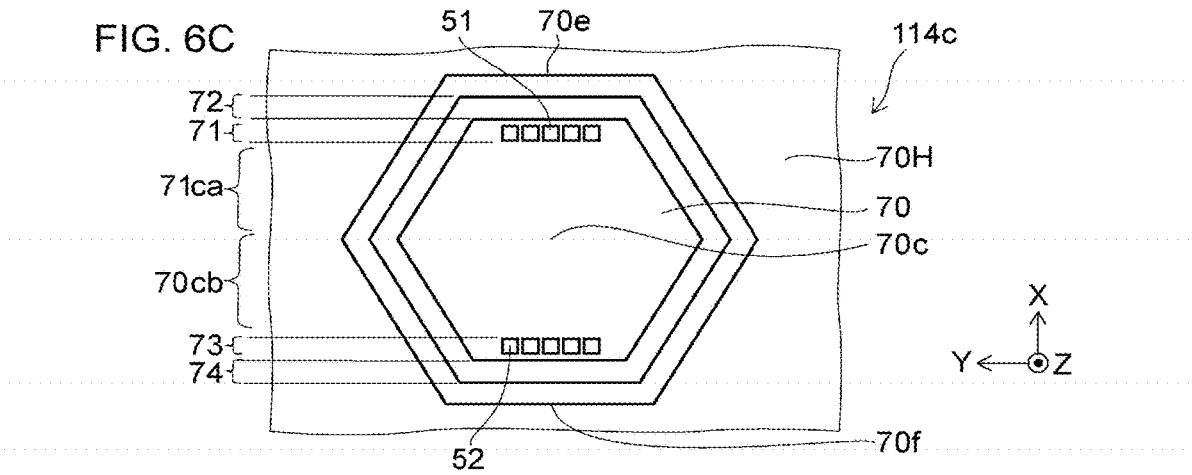

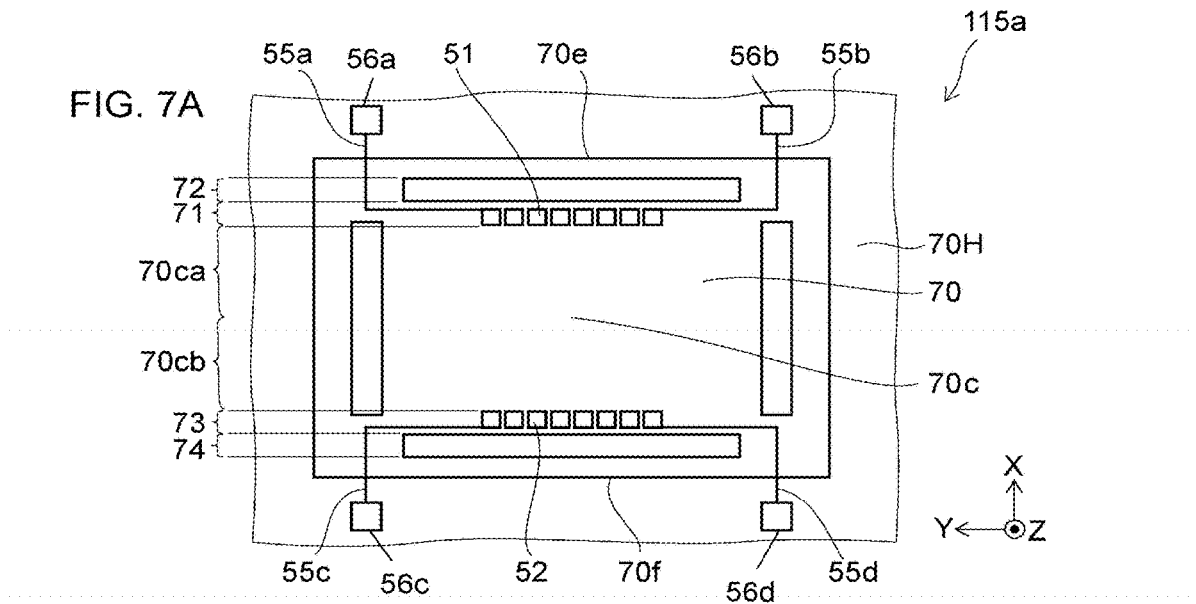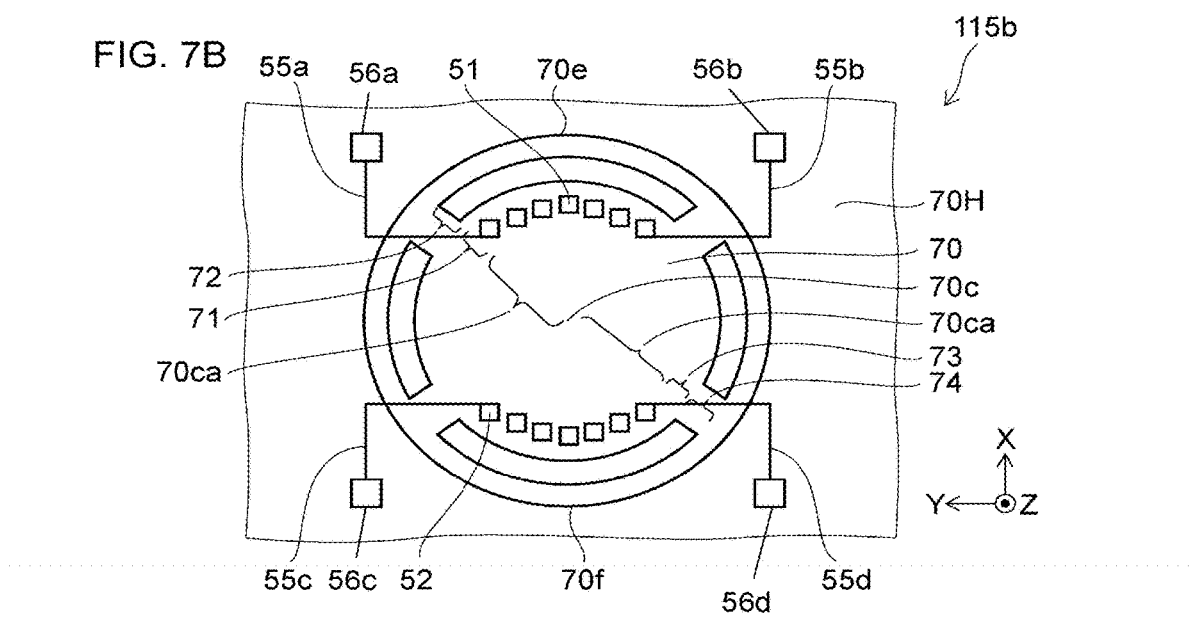

PRESSURE SENSOR, MICROPHONE, ULTRASONIC SENSOR, BLOOD PRESSURE SENSOR, AND TOUCH PANEL

CROSS-REFERENCE TO RELATED APPLICATION

This application is based upon and claims the benefit of priority from the prior Japanese Patent Application No. 2015-177999, filed on Sep. 9, 2015, the entire contents of which are incorporated herein by reference.

FIELD

Embodiments described herein relate generally to a pressure sensor, a microphone, an ultrasonic sensor, a blood pressure sensor and a touch panel.

BACKGROUND

A pressure sensor using a Micro Electro Mechanical Systems (MEMS) technology is known. The pressure sensor can be applied to a microphone, an ultrasonic sensor, a blood pressure sensor, a touch panel etc. A pressure sensor using a magnetic spin technology is also proposed. Such a pressure sensor is desired to have enhanced sensitivity.

BRIEF DESCRIPTION OF THE DRAWINGS

FIG. 3A is a schematic perspective view which illustrates a simulation model of a membrane part of the pressure sensor,
and FIG. 3B is a graph which illustrates simulation results;
FIG. 4A is a schematic perspective view which illustrates a simulation model of a membrane part of the pressure sensor,
and FIG. 4B is a graph which illustrates simulation results;
FIG. 5 is a schematic perspective view to explain a modified example of a membrane part of a pressure sensor;
FIGS. 6A to 6C are schematic plane views which illustrate modified examples of the pressure sensor of the first embodiment;
FIGS. 7A and 7B are schematic plan views which illustrate other modified examples of the pressure sensor of the first embodiment.

DETAILED DESCRIPTION

Figure 1A:
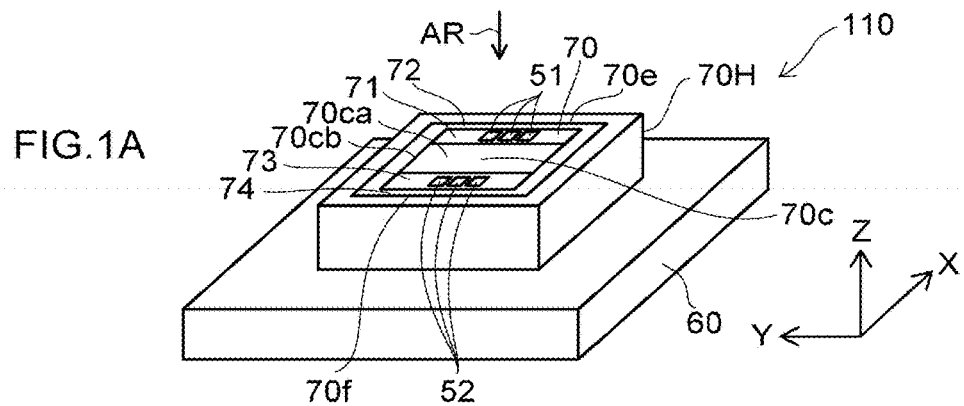
FIGS. 1A to 1E are schematic diagrams which illustrate a pressure sensor according to a first embodiment.

According to one embodiment, a pressure sensor which includes a support portion, a transformable membrane part and a first sensor portion is provided. The membrane part includes a first end portion supported by the support portion, a first area and a second area. The first area is positioned between a center of the membrane part and the first end portion, and has a first rigidity. The second area is positioned between the first area and the first end portion, and has a second rigidity lower than the first rigidity. The first sensor portion is provided at the first area, and includes a first magnetic layer, a second magnetic layer and a first intermediate layer provided between the first magnetic layer and the second magnetic layer. In the a pressure sensor, a first end-side distance between the first area and the first end portion is shorter than a first center-side distance between the second area and the center of the membrane part.

Hereinafter, further embodiments will be described with reference to the drawings. In the drawings, the same reference numerals denote the same or similar portions respectively.

Each drawing is a schematic or conceptual illustration, and a relation between a thickness and a width of each portion, a ratio between sizes of portions etc. are not necessarily the same as actual ones.

Even in a case where the same portion is illustrated, the size or the ratio may be differently illustrated according to drawings.

Figure 1B:
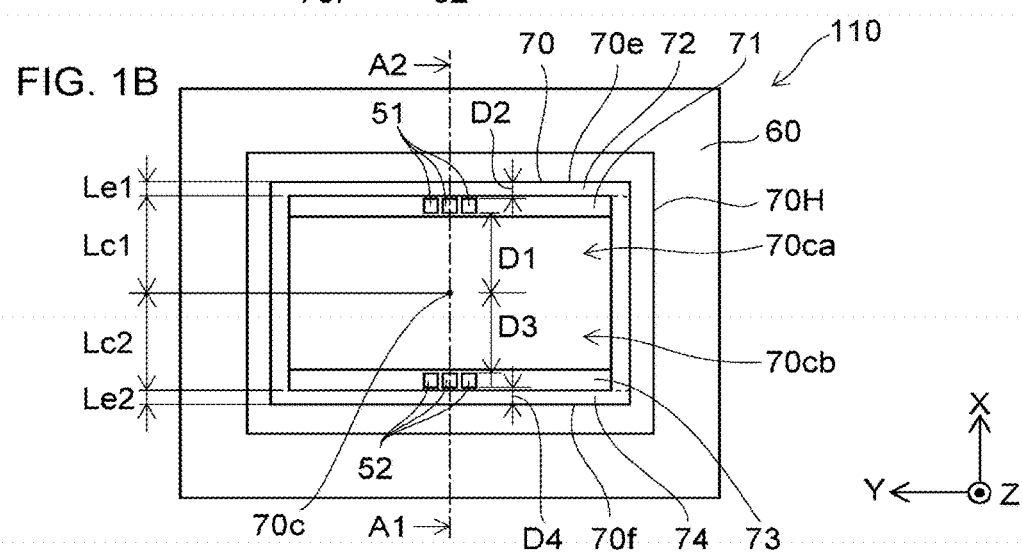
Figure 1C:
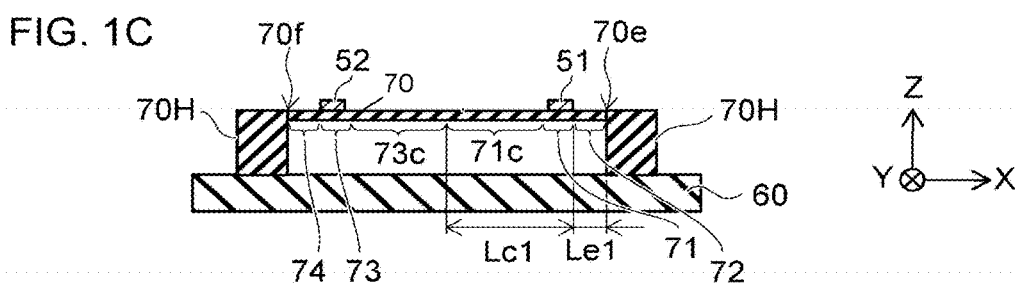
Figure 1D:
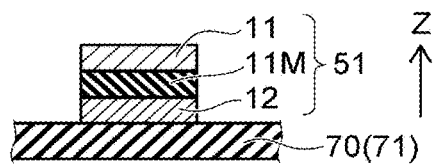
Figure 1E:
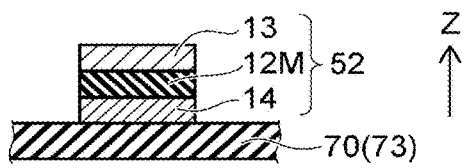

FIGS. 1A to 1E are schematic diagrams which illustrate a pressure sensor according to a first embodiment. FIG. 1A is a perspective view and FIG. 1B is a plan view when seen in a direction of an arrow AR illustrated in FIG. 1A. FIG. 1C is a cross-sectional view taken along a surface A1-A2 illustrated in FIG. 1B. FIGS. 1D and 1E are diagrams which respectively illustrate cross-sections of first and second sensor portions illustrated in FIG. 1C in an enlarged scale.

As illustrated in FIGS. 1A to 1C, the pressure sensor 110 according to the embodiment includes a support portion 70H having a rectangular frame shape, a membrane part 70, a plurality of first sensor portions 51, and a plurality of second sensor portions 52. The support portion 70H is provided on a substrate 60. A peripheral portion of the membrane part 70 is supported by the support portion 70H. On the membrane part 70, the first sensor portions 51 and the second sensor portions 52 are arranged. The membrane part 70 is arranged between the first sensor portions 51 and the second sensor portions 52 and the substrate 60.

The membrane part 70 has flexibility and can be transformed. The membrane part 70 includes a first end portion 70e, a first area 71, a second area 72, a second end portion 70f, a third area 73, and a fourth area 74. A width of the second area 72 in the vertical direction in FIG. 1B is a first end-side distance Le1 between the first area 71 and the first end portion 70e. A width of the fourth area 74 in the vertical direction in FIG. 1B is a second end-side distance Le2 between the third area 73 and the second end portion 70f.

The first end portion 70e and the second end portion 70f are supported by the support portion 70H. A center 70c of the membrane part 70 is set between the first end portion 70e and the second end portion 70f.

The center 70c of the membrane part 70 is the center of an area of the membrane part 70 which can be transformed. The center 70c of the membrane part 70 may be the center of an area which can be transformed.

The first area 71 is positioned between the center 70c and the first end portion 70e. The first area 71 has first rigidity.

The second area 72 is positioned between the first area 71 and the first end portion 70e. The second area 72 borders the first end portion 70e. The second area 72 has second rigidity. The second rigidity is lower than the first rigidity, for example.

The third area 73 is positioned between the center 70c and the second end portion 70f. The third area 73 has third rigidity. The third rigidity may be substantially the same as the first rigidity or may be different from the first rigidity.

The fourth area 74 is positioned between the third area 73 and the second end portion 70f. The fourth area 74 borders the second end portion 70f. The fourth area 74 has fourth rigidity. The fourth rigidity is lower than the third rigidity, for example.

In the embodiment, the "rigidity" may be bending rigidity, specifically, bending rigidity of a "flat plate", and more specifically, bending rigidity of a "plate of a corrugated shape". The "rigidity" represents a degree of difficulty in bending transformation. The "rigidity" is determined based on a cross-sectional shape of an object and physical properties of the object. For example, the "rigidity" i.e. bending rigidity D (N·m (Newton meter)) of a flat plate is simply represented as $E \times h^3/(12 \times (1-v^2))$ using a thickness h (meter) of the object, a Young's modulus E of the object, and a Poisson's ratio v of the object.

The first sensor portions 51 are provided on the first area 71. The second sensor portions 52 are provided on the third area 73.

For example, the membrane part 70 further includes a first center-side area 70ca. The first center-side area 70ca is provided between the center 70c and the first area 71. Between the first center-side area 70ca and the second area 72, the first area 71 is provided.

Between the center 70c of the membrane part 70 and the first area 71, an area in which the first sensor portions 51 are not provided corresponds to the first center-side area 70ca.

The membrane part 70 further includes a second center-side area 70cb. The second center-side area 70cb is provided between the center 70c and the third area 73. Between the second center-side area 70cb and the fourth area 74, the third area 73 is provided.

Between the center 70c of the membrane part 70 and the third area 73, an area in which the second sensor portions 52 are not provided corresponds to the second center-side area 70cb.

As illustrated in FIG. 1D, the first sensor portion 51 includes a first magnetic layer 11, a second magnetic layer 12, and a first intermediate layer 11M which is provided between the first magnetic layer 11 and the second magnetic layer 12. A material of the first intermediate layer 11M will be described below.

The electric resistance between the first magnetic layer 11 and the second magnetic layer 12 changes according to transformation of the membrane part 70. When pressure is applied to the pressure sensor 110, a stress is applied to the membrane part 70 in accordance with the pressure. According to the stress, the membrane part 70 is transformed. In accordance with the transformation of the membrane part 70, based on an inverse magnetostrictive effect, at least one of the magnetization of the first magnetic layer 11 and the magnetization of the second magnetic layer 12 changes. More specifically, a change in the magnetization occurs based on the inverse magnetostrictive effect due to an anisotropic strain generated in the first sensor portions 51. In addition to the applied pressure, an angle between the magnetization of the first magnetic layer 11 and the magnetization of the second magnetic layer 12 changes. In accordance with the change in the angle, the electric resistance between the first magnetic layer 11 and the second magnetic layer 12 changes. By observing the change in the electric resistance, pressure applied to the pressure sensor 110 can be detected.

As illustrated in FIG. 1E, each of the second sensor portions 52 includes a third magnetic layer 13, a fourth magnetic layer 14, and a second intermediate layer 12M provided between the third magnetic layer 13 and the fourth magnetic layer 14. The electric resistance between the third magnetic layer 13 and the fourth magnetic layer 14 changes with transformation of the membrane part 70 in each of the second sensor portions 52. With transformation of the membrane part 70, a change in the magnetization occurs based on the inverse magnetostrictive effect, resulting in change of the electric resistance changes. More specifically, change in the magnetization occurs based on the inverse magnetostrictive effect according to an anisotropic strain generated in the second sensor portions 52. According to the change in the magnetization, the electric resistance between the third magnetic layer 13 and the fourth magnetic layer 14 changes.

In the embodiment, a distance between the first sensor portions 51 and the center 70c of the membrane part 70 i.e. a first distance D1 is larger than a distance between the first sensor portions 51 and the first end portion 70e i.e. a second distance D2. The first sensor portions 51 are arranged near the first end portion 70e. The first sensor portions 51 are arranged far from the center 70c of the membrane part 70.

The first end-side distance Le1 between the first area 71 and the first end portion 70e is smaller than a first center-side distance Lc1 between the second area 72 and the center 70c.

In the embodiment, a distance between the second sensor portions 52 and the center 70c i.e. a third distance D3 is larger than a distance between the second sensor portions 52 and the second end portion 70f i.e. a fourth distance D4. The second sensor portions 52 are arranged near the second end portion 70f. The second sensor portions 52 are arranged far from the center 70c of the membrane part 70.

The second end-side distance Le2 between the third area 73 and the second end portion 70f is smaller than a second center-side distance Lc2 between the fourth area 74 and the center 70c.

In this manner, the second area 72 having relatively low rigidity is provided near the first end portion 70e, and the first area 71 having relatively high rigidity is arranged between the second area 72 and the center 70c of the membrane part 70. On the first area 71, the first sensor portions 51 are provided. By disposing the second area 72 having relatively low rigidity, the membrane part 70 is greatly transformed. As a result, a large strain i.e. an anisotropic strain is generated in the first area 71. By the large strain, a large stress is applied to the first sensor portions 51, and high sensitivity can be obtained in the first sensor portions 51.

Similarly, the fourth area 74 having relative low rigidity is provided near the second end portion 70f, and the third area 73 having relative high rigidity is arranged between the fourth area 74 and the center 70c of the membrane part 70. The second sensor portions 52 are provided on the third area 73. By disposing the fourth area 74 having relatively low rigidity, a large transformation of the membrane part 70 is acquired. As a result, a large strain i.e. an anisotropic strain is generated in the third area 73. According to the large strain, a large stress is applied to the second sensor portions 52, and a high sensitivity of the second sensor portions 52 is obtained.

A direction from the center 70c of the membrane part 70 toward the first end portion 70e may be referred to as a first direction. The first direction may be expressed as an X-axis direction, one axis perpendicular to the X-axis direction may be expressed as a Z-axis direction, and a direction perpendicular to the X-axis direction and the Z-axis direction may be expressed as a Y-axis direction.

A direction from the membrane part 70 toward the first sensor portions 51, in other words, a direction from the first area 71 toward the first sensor portions 51 may be referred to as a second direction. The second direction may correspond to the Z-axis direction.

The second end portion 70f extends in the first direction i.e. the X-axis direction in parallel with the first end portion 70e.

At least a part of the second sensor portions 52 may be arranged separately from at least a part of the first sensor portions 51 in the X-axis direction. In addition, between at least a part of the second sensor portions 52 and a part of the first sensor portions 51, the center 70c of the membrane part 70 may be positioned.

In the embodiment, the shape of the membrane part 70 is substantially a rectangle. Along four outer edges of the rectangle, the second area 72 and the fourth area 74 are provided.

The first sensor portions 51 are arranged to be aligned in parallel with one long side of the rectangle. The second sensor portions 52 are arranged to be aligned in parallel with the other long side of the rectangle. The first sensor portions 51 and the second sensor portions 52 may only be arranged to be aligned along the long sides of the rectangle, for example, in opposition to the long sides of the rectangle with a distance provided.

In the embodiment, while the membrane part 70 is arranged between the first and second sensor portions 51, 52 and the substrate 60, the first sensor portions 51 and the second sensor portions 52 may be arranged between at least a part of the membrane part 70 and the substrate 60.

As illustrated in FIG. 1C, the membrane part 70 is separate from the substrate 60, and a space is formed between the membrane part 70 and the substrate 60. Gas or liquid such as air may be provided in the space.

In the embodiment, the second rigidity of the second area 72 and the third area 73 is lower than the first rigidity of the first area 71 and the fourth area 74. In such a case, the magnitude of the rigidity may be set to a desired degree by selecting a thickness of the membrane part 70 or a material and a cross-sectional shape of the membrane part 70. Hereinafter, modified examples configured to change rigidity will be described.

Figure 2A:
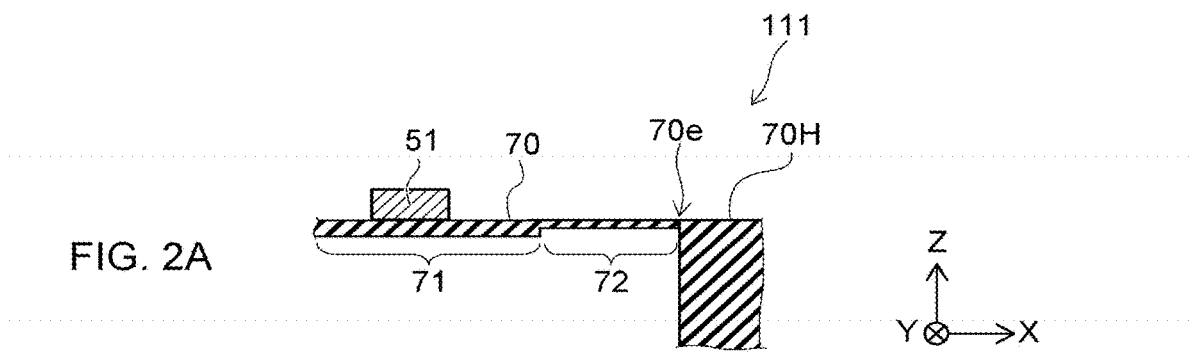
FIGS. 2A to 2C are schematic diagrams which illustrate modified examples of the cross-sectional shape of a part of the pressure sensor.
Figure 2B:
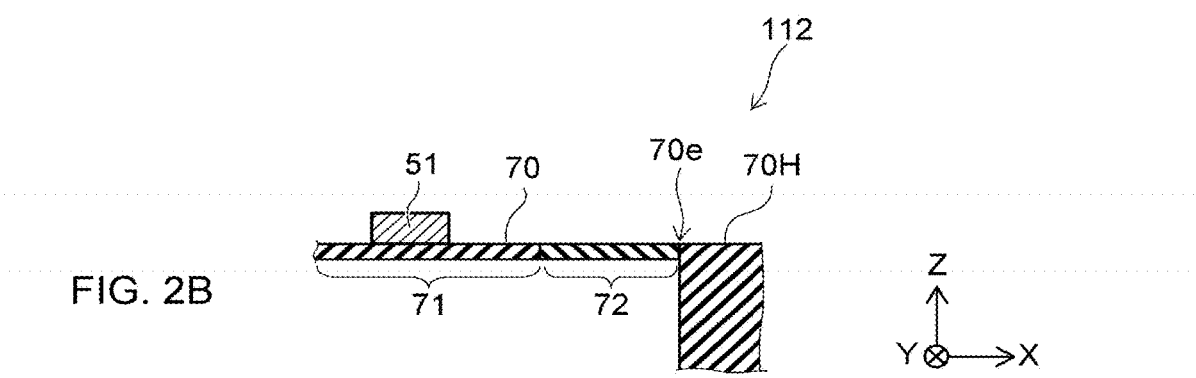
Figure 2C:
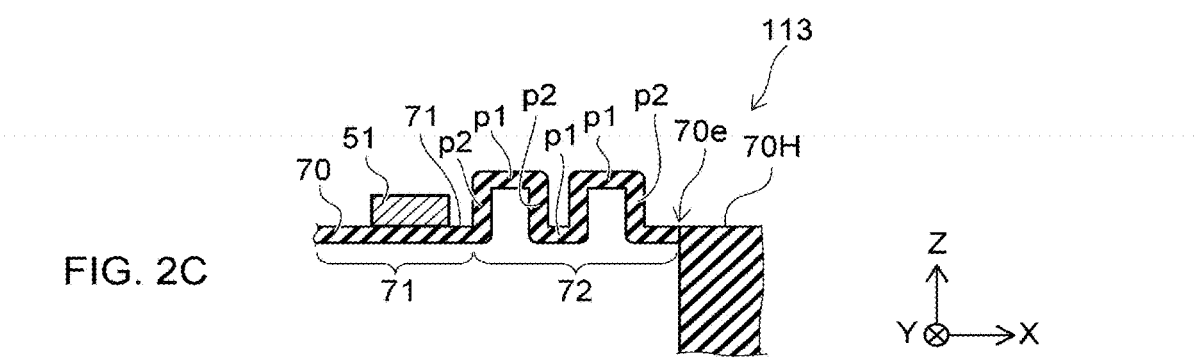

FIGS. 2A to 2C are schematic cross-sectional views of modified examples of a part of the pressure sensor according to the first embodiment. The diagrams illustrate portions corresponding to a portion including the first area 71 and the second area 72 of the membrane part 70 which are illustrated in FIGS. 1A to 1C. A portion corresponding to a portion including the third area 73 and the fourth area 74 of the membrane part 70 may be similarly configured.

In a pressure sensor 111 illustrated in FIG. 2A, a thickness of the second area 72 i.e. a length of the second area 72 along the Z-axis direction is smaller or thinner than a thickness of the first area 71 i.e. a length of the first area 71 along the Z-axis direction.

In such a case, the material of the membrane part 70 is the same in all the areas. For example, a thickness of the second area 72 may be 0.8 times of a thickness of the first area 71 or less. By configuring the thickness of the second area 72 to be 0.8 times of the thickness of the first area 71 or less, the rigidity of the second area 72 is ½ of the rigidity of the first area 71 or less, and the second area 72 is easily transformable. When the thickness of the second area 72 is configured to be excessively thin, the mechanical strength is low, and the thickness of a certain degree of the second area 72 is necessary. As the material of the membrane part 70, at least one of single-crystal silicon, amorphous silicon, polysilicon, silicon oxide, silicon nitride, and aluminum oxide may be used.

In the pressure sensor 112 illustrated in FIG. 2B, the Young's modulus of the second area 72 is lower than the Young's modulus of the first area 71, and thus, the second area 72 is easily transformable. Desirably, an anisotropic Young's modulus is arranged in the second area 72. In the anisotropic Young's modulus, a Young's modulus in a direction along a surface of the second area 72 i.e. a portion of a film surface of the membrane part 70 is lower than a Young's modulus in a direction perpendicular to a surface of the second area 72 i.e. a portion of a film surface of the membrane part 70. By configuring the Young's modulus i.e. the anisotropic Young's modulus of the second area 72 to be lower than the Young's modulus of the first area 71, the second rigidity of the second area 72 can be lower than the first rigidity of the first area 71. As the material of the first area 71, single-crystal silicon, amorphous silicon, polysilicon, silicon oxide, silicon nitride, aluminum oxide etc. may be used. In such a case, as the material of the second area 72, a resin containing xylylene such as a poly-para-xylylene resin etc. may be used. By configuring the Young's modulus of the second area 72 to be lower than the Young's modulus of the first area 71, the second area 72 is easily transformable.

In a pressure sensor 113 illustrated in FIG. 2C, the second area 72 has a corrugated shape. The second area 72 includes a plurality of first portions p1 and a plurality of second portions p2. The second portions p2 are alternately connected to the first portions p1. The first portions p1 extend in the first direction, in other words, in the X-axis direction from the center 70c of the membrane part 70 toward the first end portion 70e. The second portions p2 extend in the second direction. The second direction is a direction of the thickness of the membrane part 70, in other words, the Z-axis direction from the membrane part 70 i.e. the first area 71 toward the first sensor portions 51.

In this manner, in the second area 72, the first portions p1 and the second portions p2 which have mutually-different extending directions are provided. According to such a structure, the second area 72 is easily transformable.

The number of the first portions p1 may be either an odd number or an even number. The number of the second portions p2 may be either an odd number or an even number.

In a case where the second area 72 has a corrugated shape as illustrated in FIG. 2C, the thickness of the first portion p1 and the second portion p2 of the second area 72 may be the same as the thickness of the first area 71.

By configuring the thickness of the first portions p1 and the second portions p2 of the second area 72 so as to be substantially the same as the thickness of the first area 71, the membrane part 70 including the first area 71 and the second area 72 can be easily formed.

In the pressure sensors 111, 112, and 113, a first end-side distance Le1 between the first areas 71 and the first end portion 70e is shorter than a first center-side distance Lc1 between the second areas 72 and the center 70c of the membrane part 70. According to such settings, high sensitivity of each first sensor portion 51 is acquired.

Figure 3A:
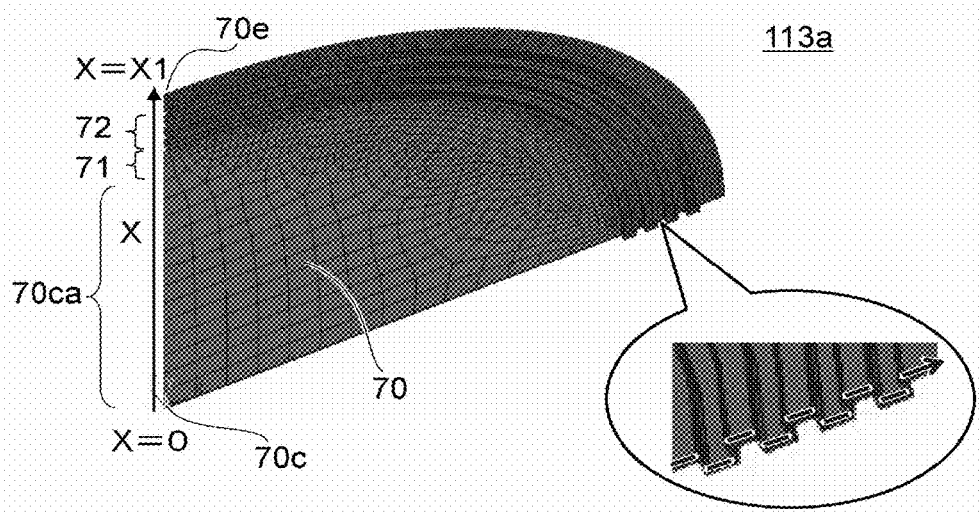
FIGS. 3A and 3B are diagrams to explain sensitivity characteristics of a pressure sensor.
Figure 3B:
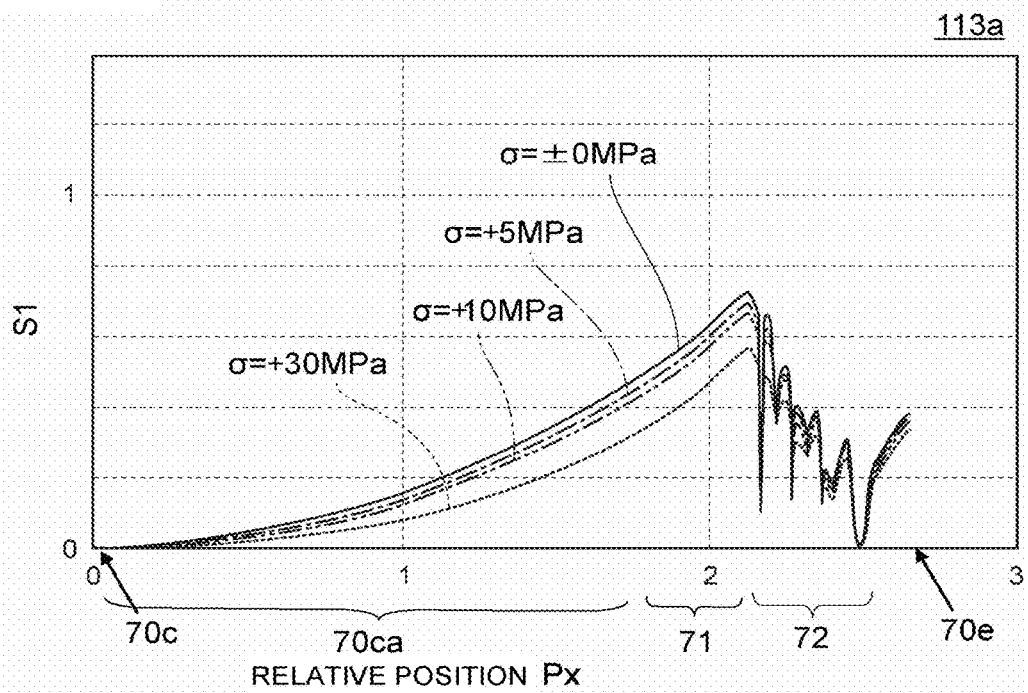

Hereinafter, sensitivity characteristics of the pressure sensors will be described. FIGS. 3A and 3B are diagrams to explain sensitivity characteristics of a modified example of the pressure sensor according to the first embodiment. FIG. 3A is a schematic perspective view which illustrates a simulation model of a ¼ portion of a membrane part of the pressure sensor. FIG. 3B is a graph which illustrates simulation results. In FIG. 3A, a corrugated structure is illustrated with an enlarged portion of the corrugated structure.

In the simulation, the shape of a membrane part 70 of a pressure sensor 113a is a circle. The direction of the diameter of the circle corresponds to the X-axis direction. The membrane part 70 is formed using an aluminum oxide film. The Young's modulus of the membrane part 70 is 120 GPa, and the Poisson's ratio of the membrane part 70 is 0.24. In the second area 72 of the membrane part 70, a corrugated structure is arranged. A distance between the center 70c of the membrane part 70 and the second area 72 is about ⅘ of the radius of the membrane part 70. A width of the second area 72 which is a distance between the second area 72 and the first end portion 70e is about ⅕ of the radius of the membrane part 70.

In the corrugated structure of the second area 72, the number of corrugations is four. The corrugated structure is configured by a combination of two first portions p1 and two second portions p2. The strength of the corrugations i.e. the ratio of the height to the thickness of the corrugations is five.

FIG. 3B illustrates an example of an "anisotropic strain slope" of the membrane part 70 when the membrane part 70 is formed with a film stress σ. In this example, a pressure ±1 Pa having a sound pressure level (SPL) of 94 dB is applied to the membrane part 70 illustrated in FIG. 3A. In FIG. 3B, the horizontal axis represents a relative position Px in the X-axis direction, and the vertical axis represents the anisotropic strain slope S1. The anisotropic strain slope S1 is a change rate of the anisotropic strain with respect to applied pressure in the range of the applied pressure of ±1 Pa. The anisotropic stress is a difference between a maximum principal strain i.e. a first strain in a direction in which the strain is a maximum and a minimum principal strain i.e. a second strain in a direction in which the strain is a minimum and in a direction perpendicular to the direction of the first strain. As the anisotropic strain slope S1 becomes larger, the sensitivity increases. In FIG. 3B, the anisotropic strain slope S1 is represented as a relative value.

In FIG. 3B, results of simulations at the times when a film stress σ of the membrane part 70 is ±0 MPa, +5 MPa, +10 MPa and +30 MPa are illustrated.

As illustrated in FIG. 3B, in the pressure sensor 113a a large anisotropic strain slope S1 can be obtained in the range in which the relative position Px in the X-axis direction is 1.8 or more and 2.2 or less. By arranging the first sensor portions 51 in the area of the membrane part 70 of the range, high sensitivity is acquired.

As can be understood from FIG. 3B, in the pressure sensor 113a a large anisotropic strain slope S1 can be obtained even when the membrane part 70 has different film stresses σ such as ±0 MPa, +5 MPa, +10 MPa and +30 MPa. The pressure sensor 113a is robust for the film stress σ.

Figure 4A:
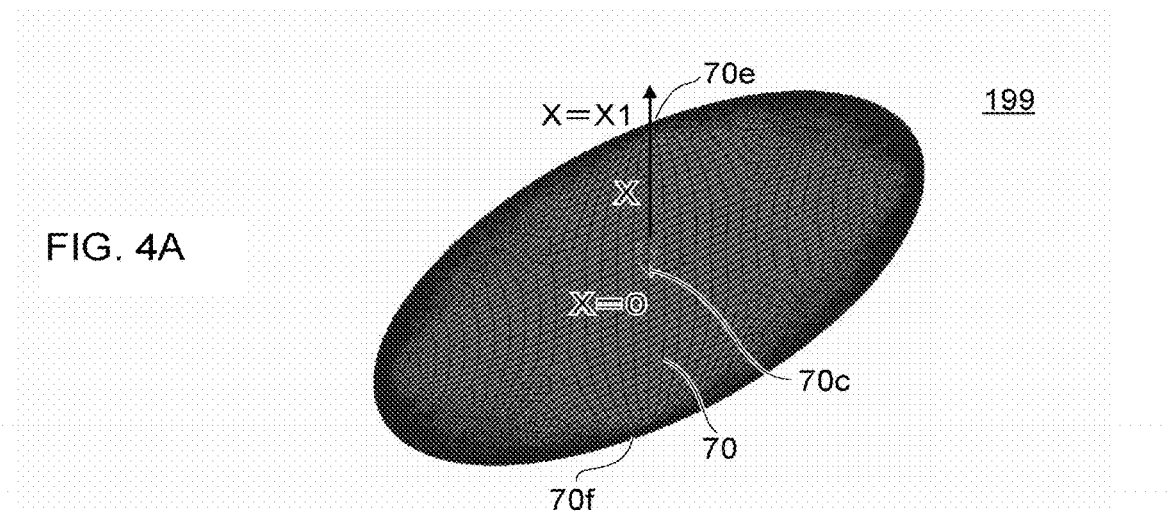
FIGS. 4A and 4B are diagrams to explain sensitivity characteristics of another pressure sensor.
Figure 4B:
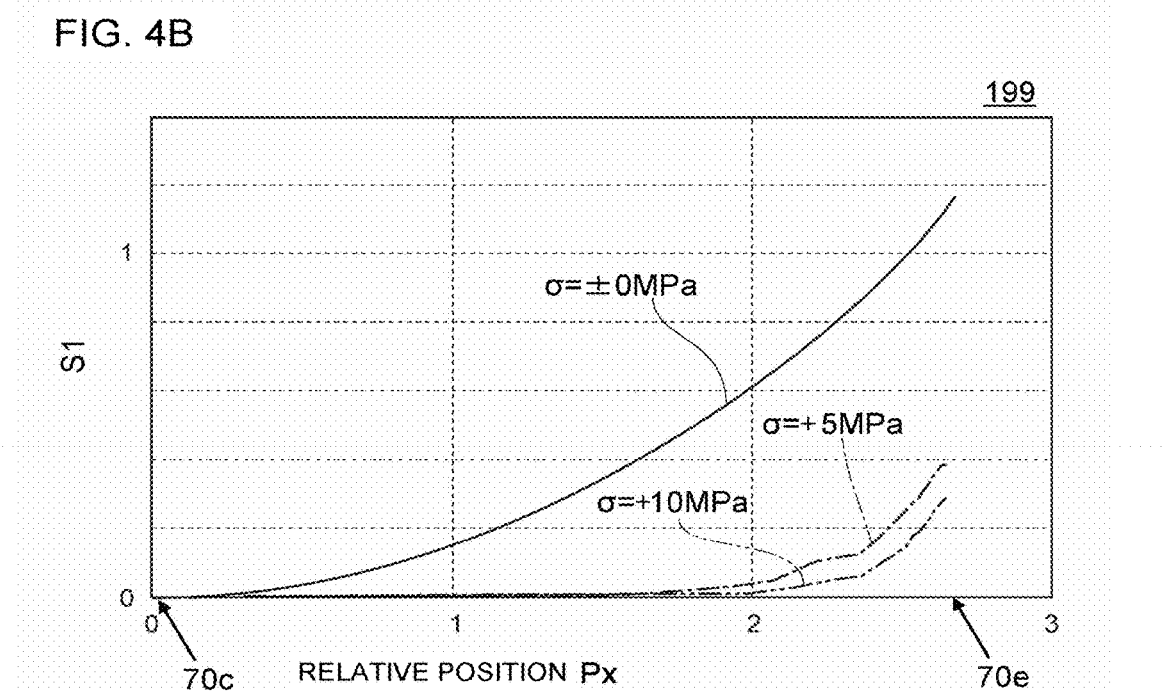

FIGS. 4A and 4B are diagrams to explain sensitivity characteristics of another modified example of the pressure sensor according to the first embodiment. FIG. 4A is a schematic perspective view which illustrates a simulation model of a circular membrane part. FIG. 4B is a graph which illustrates simulation results.

In FIG. 4A, a pressure sensor 199 has a circular membrane part 70. In the membrane part 70, an area corresponding to the second area 72 of FIG. 1B is not arranged, and the thickness, the material, the shape etc. of the membrane part 70 are uniform over the whole membrane part 70 approximately.

As illustrated in FIG. 4B, in the pressure sensor 199, a relatively large anisotropic strain slope S1 can be obtained, when the film stress σ is ±0 MPa. However, when the film stress σ is +5 MPa or +10 MPa, the anisotropic strain slope S1 is markedly small. Thus, when the membrane part 70 has a film stress σ as caused actually in a manufacturing process of the membrane part 70, sufficient sensitivity cannot be attained.

The pressure sensor 113a illustrated in FIG. 3A can attain a sensitivity higher than that of the pressure sensor 199 illustrated in FIG. 4A.

The pressure sensors 111, 112 illustrated in FIGS. 2A and 2B can obtain a large anisotropic strain slope S1, when the film stress σ is ±0 MPa, +5 MPa, +10 MPa or +30 MPa.

According to the first embodiment and the modified examples of the first embodiment described above, pressure sensors which are robust for the film stress σ of the membrane part 70 and have high sensitivity can be provided.

In the first embodiment, magnetic bodies are used in the first sensor portions 51 and the second sensor portions 52, and applied pressure is detected based on the inverse magnetostrictive effect. When an area having a high anisotropic strain slope is large, high sensitivity is acquired. By arranging the first area 71 and the second area 72 having mutually-different rigidity and arranging sensor portions in the first area 71, a high anisotropic strain slope in a large area is acquired.

A silicon piezoresistance element can be used instead of the magnetic bodies in the pressure sensors. In such a case, by configuring a pressure sensor using a silicon piezoresistance element so as to have a corrugated structure, an effect of relieving film stress is obtained. However, such a pressure sensor cannot indicate sufficient sensitivity, even when the anisotropic strain slope is high and the area having a high anisotropic strain slope is large.

In the first embodiment, the support portion 70H may be formed using a silicon substrate. The membrane part 70 may be formed using at least one of single-crystal silicon, amorphous silicon, polysilicon, silicon oxide, silicon nitride, silicon oxynitride, and aluminum oxide.

In a case where the second magnetic layer 12 illustrated in FIG. 1D is a magnetization fixed layer, for example, an Co—Fe—B alloy may be used for the second magnetic layer 12. As the second magnetic layer 12, an $(Co_xFe1-x)1-yBy$ alloy ($0 \le x \le 1$, $0 \le y \le 0.3$) may be used. In the formula, x and y are atomic percent. As the second magnetic layer 12, a Fe—Co alloy may be used.

The first intermediate layer 11M can separate magnetic coupling between the first magnetic layer 11 and the second magnetic layer 12. The first intermediate layer 11M may be formed using metal, an insulating body, or semiconductor. The metal may contain at least one of Cu, Au, and Ag. The insulating body or the semiconductor described above may contain at least one of magnesium oxide, aluminum oxide, titanium oxide, zinc oxide, and gallium oxide. The first intermediate layer 11M may include a current-confined-path (CCP) spacer layer. In a case where the CCP spacer layer is used as the first intermediate layer 11M, the first intermediate layer 11M may include an insulating layer such as an aluminum oxide layer and a metal path, for example, of Cu passing through the insulating layer.

In a case where the first magnetic layer 11 is a magnetization free layer, the first magnetic layer 11 may be formed using a ferromagnetic layer. The first magnetic layer 11 may be formed using an alloy including one of a FeCo alloy, a NiFe alloy, and Fe and Co. More specifically, a Co—Fe—B alloy, a Fe—Co—Si—B alloy, a Fe—Ga alloy, a Fe—Co—Ga alloy, a Tb-M-Fe alloy, a Tb-M1-Fe-M2 alloy, a Fe-M3-MB alloy, Ni, Fe—Al, or ferrite may be used. The Fe—Ga alloy, the Fe—Co—Ga alloy, the Tb-M-Fe alloy, the Tb-M1-Fe-M2 alloy, the Fe-M3-MB alloy, Ni, Fe—Al, and ferrite have a large magnetostriction constant.

The planar shape of the membrane part 70 described above is a rectangle, but the planar shape may be a square, a polygonal, a circle, an elongated circular shape etc.

The substrate 60 may be formed using an organic material such as a resin, or an inorganic material such as a ceramic.

FIG. 5 is a diagram which illustrates a modified example of the membrane part of the pressure sensor according to the first embodiment, and is also a schematic perspective view to show a simulation model of a ¼ part of the membrane part 70. In FIG. 5, a corrugated structure is illustrated with an enlarged portion of the corrugated structure. As illustrated in FIG. 5, in a pressure sensor 113b, the shape of the membrane part 70 is substantially rectangle, and a second area 72 has a corrugated structure. The second area 72 is provided along four outer edges of the rectangle of the membrane part 70. The pressure sensor 113b can provide a pressure sensor having high sensitivity.

FIGS. 6A to 6C are schematic plane views which illustrate modified examples of the pressure sensor according to the first embodiment.

As illustrated in FIG. 6A, in a pressure sensor 114a, the planar shape of a membrane part 70 is substantially a rectangle. In the membrane part 70, a first area 71 and a second area 72 extending along the Y-axis direction, and a third area 73 and a fourth area 74 extending along the Y-axis direction are arranged.

A plurality of first sensor portions 51 are provided to be aligned along the Y-axis direction on the first area 71. At least two of the first sensor portions 51 may be arranged to be aligned along the Y-axis direction.

A plurality of second sensor portions 52 are provided to be aligned along the Y-axis direction on the third area 73. At least two of the second sensor portions 52 may be arranged to be aligned along the Y-axis direction. A center 70c of the membrane part 70 is positioned between at least a part of the second sensor portions 52 and at least a part of the first sensor portions 51.

In the membrane part 70, a direction from the first area 71 toward the first sensor portions 51 is a stacking direction i.e. a Z-axis direction. One direction perpendicular to the stacking direction is a first in-plane direction. A direction perpendicular to the stacking direction and the first in-plane direction is a second in-plane direction. For example, the first in-plane direction is the X-axis direction i.e. a first direction, and the second in-plane direction is the Y-axis direction i.e. a second direction.

A first length d1 of the membrane part 70 along the first in-plane direction i.e. the X-axis direction is shorter than a second length d2 of the membrane part 70 along the second in-plane direction i.e. the Y-axis direction. The membrane part 70 includes a first side s1 and a second side s2. The first side s1 extends in the first in-plane direction i.e. the X-axis direction. The second side s2 extends in the second in-plane direction i.e. the Y-axis direction. The first side s1 is a short side, and the second side s2 is a long side. The second area 72 extends in parallel with the second side s2. A length of the second area 72 in a direction along the second side s2 i.e. the Y-axis direction is longer than a length of the second area 72 in a direction along the first side s1 i.e. the X-axis direction.

A length of the fourth area 74 in a direction along the second side s2 i.e. the Y-axis direction is longer than a length of the fourth area 74 in a direction along the first side s1 i.e. the X-axis direction.

The first area 71 is provided between the second area 72 and the center 70c of the membrane part 70. The first area 71 extends along the second side s2. A length of the first area 71 in a direction along the second side s2 i.e. the Y-axis direction is longer than a length of the first area 71 in a direction along the first side s1 i.e. X-axis direction.

The third area 73 is provided between the fourth area 74 and the center 70c of the membrane part 70. The third area 73 extends along the extending direction of the second side s2. A length of the third area 73 in a direction along the second side s2 i.e. the Y-axis direction is longer than a length of the third area 73 in a direction along the first side s1 i.e. the X-axis direction.

In a case where the length of the first side s1 and the length of the second side s2 are different from each other, sensor portions are desirably arranged along the long side. In the membrane part 70, since a strain is high in an area along the long side, by arranging the sensor portions in an area along the long side, high sensitivity is acquired.

As illustrated in FIG. 6B, in a pressure sensor 114b, the planar shape of a membrane part 70 is substantially a circle. In the membrane part 70, a first area 71, a second area 72, a third area 73 and a fourth area 74 are arranged. The areas 71 to 74 extend respectively in a concentric circular arc form so as to surround the center 70c. A plurality of first sensor portions 51 are arranged in a circular arc form on the first area 71. A plurality of second sensor portions 52 are arranged in a circular arc form on the third area 73.

In the pressure sensor 114b, a boundary between a first end portion 70e and a support portion 70H has a curved shape. In this manner, the outer shape of the membrane part 70 may be a curved shape.

As illustrated in FIG. 6C, in a pressure sensor 114c, the planar shape of a membrane part 70 is substantially a hexagon. In the membrane part 70, a first area 71, a second area 72, a third area 73 and a fourth area 74 arranged. The areas 71 to 74 configure sides of concentric hexagons to surround the center 70c are arranged. A plurality of first sensor portions 51 are provided on the first area 71. A plurality of second sensor portions 52 are provided on the third area 73. The first sensor portions 51 are provided along a side of the first area 71 of the membrane part 70. The second sensor portions 52 are provided along a side of the third area 73 of the membrane part 70.

In the pressure sensors 114a, 114b, and 114c, the second area 72 and the fourth area 74 having rigidity lower than the first area 71 and the third area 73 are provided, and accordingly, the sensitivity is high.

In the pressure sensor 114a, the second area 72 or the fourth area 74 is arranged along the first side s1 in addition to the second side s2. The second area 72 or the fourth area 74 may be arranged along the whole outer edge of the membrane part 70.

FIGS. 7A and 7B are schematic plan views which illustrate other modified examples of the pressure sensor according to the first embodiment. As illustrated in FIG. 7A, in a pressure sensor 115a, a first conductive layer 55a, a second conductive layer 55b, a third conductive layer 55c, and a fourth conductive layer 55d are arranged. The other configurations are similar to the configurations of the pressure sensor 114a.

The first conductive layer 55a is electrically connected to a first magnetic layer 11. The second conductive layer 55b is electrically connected to a second magnetic layer 12. The third conductive layer 55c is electrically connected to a third magnetic layer 13. The fourth conductive layer 55d is electrically connected to a fourth magnetic layer 14.

Such conductive layers 55a to 55d are wirings. A portion of each conductive layer is provided on a support portion 70H. The conductive layers pass through an area which does not overlap with the second area 72 or the fourth area 74, and electrically connect portions provided on the support portion 70H, for example, pad portions 56a to 56c and the first sensor portions 51 and the second sensor portions 52, with each other.

A portion of the first conductive layer 55a overlaps with the support portion 70H in the Z-axis direction i.e. a stacking direction from the first area 71 toward the first sensor portions 51. Another portion of the first conductive layer 55a does not overlap the second area 72 in the Z-axis direction.

The second area 72 is a portion having low rigidity. The second area 72 may include a corrugated structure. The first conductive layer 55a does not pass through the second area 72 but connects the first magnetic layer 11 and a portion provided on the support portion 70H, for example, the pad portion 56a. By employing such a configuration, a stable electrical connection is obtained.

Similarly, a portion of the second conductive layer 55b overlaps with the support portion 70H in the Z-axis direction. Another portion of the second conductive layer 55b does not overlap the second area 72 in the Z-axis direction. A portion of the third conductive layer 55c overlaps with the support portion 70H in the Z-axis direction. Another portion of the third conductive layer 55c does not overlap the fourth area 74 in the Z-axis direction. A portion of the fourth conductive layer 55d overlaps with the support portion 70H in the Z-axis direction. Another portion of the fourth conductive layer 55d does not overlap the fourth area 74 in the Z-axis direction. By employing such a configuration, a stable electrical connection is acquired.

In a pressure sensor 115b illustrated in FIG. 7B, a first conductive layer 55a, a second conductive layer 55b, a third conductive layer 55c, and a fourth conductive layer 55d are arranged. In the pressure sensor 115b, the outer edge of the membrane part 70 has a curved shape. The planar shape of the membrane part 70 is substantially a circle including an elongated circular shape.

Figure 8A:
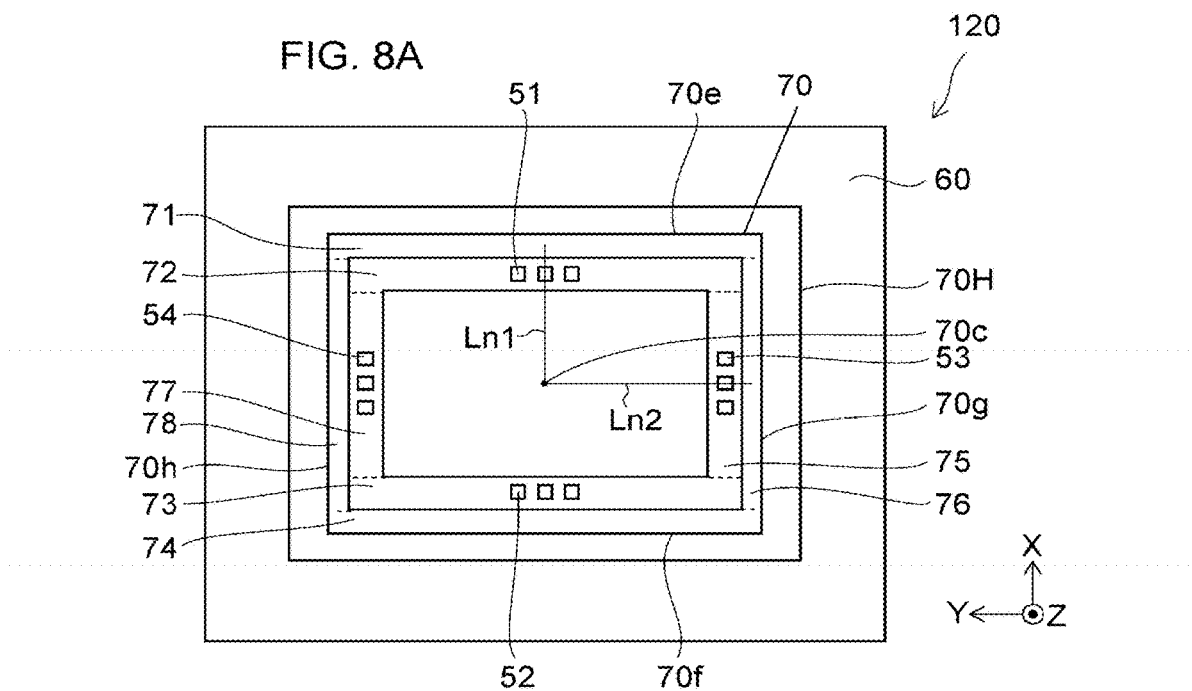
FIGS. 8A to 8C are schematic diagrams which illustrate a pressure sensors according to a second embodiment.
Figure 8B:
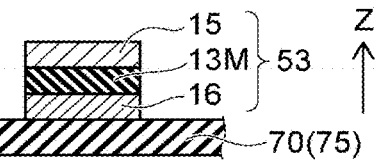
Figure 8C:
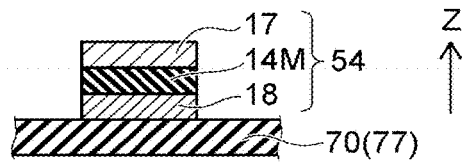

FIGS. 8A to 8C are schematic plan views which illustrate a pressure sensor according to a second embodiment. FIG. 8A is a plan view, and FIGS. 8B and 8C are cross-sectional views of sensor portions of the pressure sensor. As illustrated in FIG. 8A, the pressure sensor 120 according to the embodiment includes a support portion 70H, a membrane part 70, a plurality of first sensor portions 51, and a plurality of second sensor portions 52. Such a configuration is similar to the configuration of the pressure sensor 110 illustrated in FIGS. 1A and 1B. In the embodiment, additionally, a plurality of third sensor portions 53 and a plurality of fourth sensor portions 54 are included.

The third sensor portions 53 are provided in a fifth area 75 of the membrane part 70. The fourth sensor portions 54 are provided in a seventh area 77 of the membrane part 70.

The membrane part 70 includes a third end portion 70g, a fourth end portion 70h, a sixth area 76, and an eighth area 78.

The third end portion 70g is supported by the support portion 70H. A direction from a center 70c of the membrane part 70 toward the third end portion 70g intersects a direction from the center 70c toward a first end portion 70e. A direction form the center 70c toward the third end portion 70g, for example, is the Y-axis direction. A direction form the center 70c toward the first end portion 70e, for example, is the X-axis direction.

The fourth end portion 70h is supported by the support portion 70H. A direction from the center 70c toward the fourth end portion 70h intersects a direction from the center 70c toward the first end portion 70e. A direction form the center 70c toward the fourth end portion 70h, for example, is the Y-axis direction.

A fifth area 75 is positioned between the center 70c and the third end portion 70g. The sixth area 76 is positioned between the fifth area 75 and the third end portion 70g. A seventh area 77 is positioned between the center 70c and the fourth end portion 70h. The eighth area 78 is positioned between the seventh area 77 and the fourth end portion 70h. The third sensor portions 53 are provided on the fifth area 75. The fourth sensor portions 54 are provided on the seventh area 77.

As illustrated in FIG. 8B, each of the third sensor portions 53 includes a fifth magnetic layer 15, a sixth magnetic layer 16, and a third intermediate layer 13M provided between the fifth magnetic layer 15 and the sixth magnetic layer 16. As illustrated in FIG. 8C, each of the fourth sensor portions 54 includes a seventh magnetic layer 17, an eighth magnetic layer 18, and a fourth intermediate layer 14M provided between the seventh magnetic layer 17 and the eighth magnetic layer 18.

At least one of the magnetization of the fifth magnetic layer 15 and the magnetization of the sixth magnetic layer 16 intersects at least one of the magnetization of the first magnetic layer 11 of the first sensor portion 51 and the magnetization of the second magnetic layer 12. At least one of the magnetization of the seventh magnetic layer 17 and the magnetization of the eighth magnetic layer 18 intersects at least one of the magnetization of the first magnetic layer 11 of the first sensor portion 51 and the magnetization of the second magnetic layer 12.

The direction of the magnetization of the third sensor portions 53 is different from the direction of the magnetization of the first sensor portions 51. More specifically, the direction of the magnetization of the third sensor portions 53 is orthogonal to the direction of the magnetization of the first sensor portions 51. The direction of the magnetization of the fourth sensor portions 54 is different from the direction of the magnetization of the first sensor portions 51. More specifically, the direction of the magnetization of the fourth sensor portions 54 is orthogonal to the direction of the magnetization of the first sensor portions 51. The direction of the magnetization of the second sensor portions 52 is along the direction of the magnetization of the first sensor portions 51.

The polarity of an anisotropic strain to be applied to the first sensor portions 51 and the second sensor portions 52 is different from that to be applied to the third sensor portions 53 and the fourth sensor portions 54. By changing the direction of the magnetization of the third sensor portions 53 to the direction of the magnetization of the first sensor portions 51, detection with higher sensitivity can be performed. By changing the direction of the magnetization of the fourth sensor portions 54 to the direction of the magnetization of the first sensor portions 51, detection with higher sensitivity can be performed.

In the pressure sensor 120, the first to fourth sensor portions 51 to 54 are provided near two sides of the membrane part 70 which are perpendicular to each other. The following angle is 70 degrees or more and 110 degrees or less and, for example, is about 90 degrees. An angle is formed between a first straight line Ln1 i.e. a straight line along the X-axis direction which passes through the first sensor portion 51 and the center 70c of the membrane part 70 and a second straight line Ln2 i.e. a straight line along the Y-axis direction which passes through the third sensor portion 53 and the center 70c of the membrane part 70. The angle is 70 degrees or more and 110 degrees or less and, for example, is about 90 degrees.

Also in the pressure sensor 120, similar to the first embodiment, the second area 72 and the fourth area 74 are provided. Accordingly, the sensitivity of the pressure sensor 120 can be enhanced. In the pressure sensor 120, by respectively arranging the third sensor portions 53 and the fourth sensor portions 54 in the fifth area 75 and the seventh area 77, further higher sensitivity is acquired.

Figure 9:
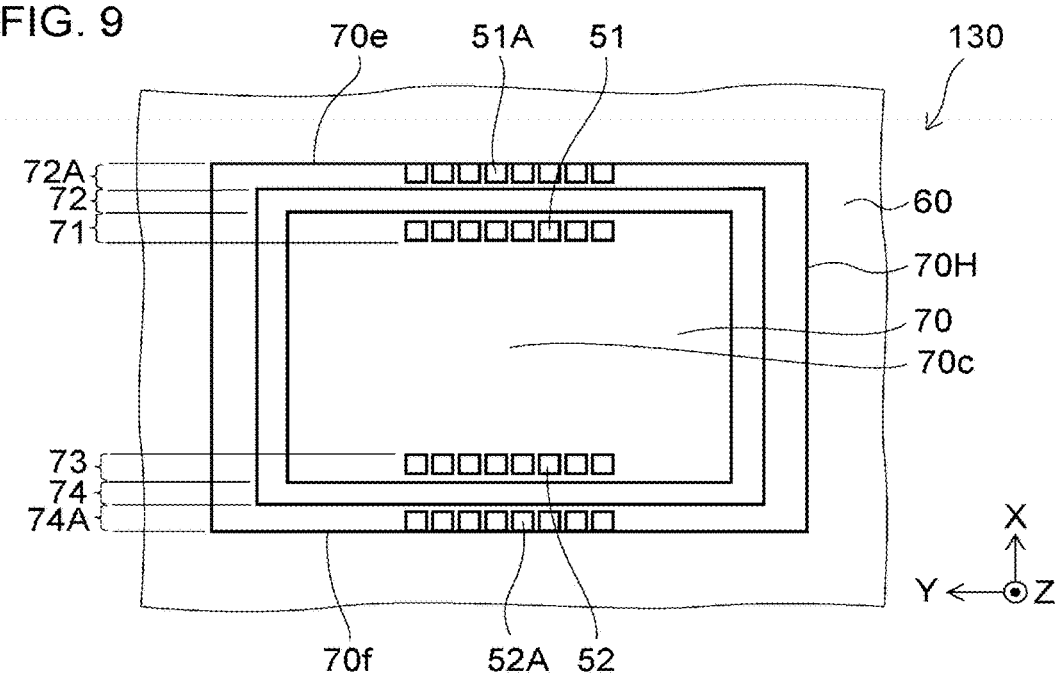
FIG. 9 is a schematic plan view which illustrates a pressure sensor according to a third embodiment.

FIG. 9 is a schematic plan view which illustrates a pressure sensor according to a third embodiment. As illustrated in FIG. 9, the pressure sensor 130 according to the embodiment includes a support portion 70H, a membrane part 70, a plurality of first sensor portions 51, a plurality of second sensor portions 52, a plurality of first end-side sensor portions 51A, and a plurality of second end-side sensor portions 52A. The membrane part 70 is transformable. The membrane part 70 includes a first end portion 70e, a first area 71, a second area 72, and a first end area 72A. The first end portion 70e is supported by the support portion 70H. The first area 71 is positioned between a center 70c of the membrane part 70 and the first end portion 70e. The second area 72 is positioned between the first area 71 and the first end portion 70e. The first end area 72A is provided between the second area 72 and the first end portion 70e.

The first sensor portions 51 of the membrane part 70 are provided on the first area 71. The first end-side sensor portions 51A of the membrane part 70 are provided on the first end area 72A.

In addition, the membrane part 70 includes a second end portion 70f, a third area 73, a fourth area 74, and a second end area 74A. The third area 73 is positioned between the center 70c of the membrane part 70 and the second end portion 70f. The fourth area 74 is positioned between the third area 73 and the second end portion 70f. The second end area 74A is provided between the fourth area 74 and the second end portion 70f.

The second sensor portions 52 are provided in the third area 73. The second end-side sensor portions 52A are provided in the second end area 74A.

The rigidity of the second area 72 is lower than the rigidity of the first area 71. The rigidity of the second area 72 is lower than the rigidity of the first end area 72A. The rigidity of the fourth area 74 is lower than the rigidity of the third area 73. The rigidity of the fourth area 74 is lower than the rigidity of the second end area 74A. In the pressure sensor 130 configured in this manner, the sensitivity of the pressure sensor can be enhanced.

Figure 10:
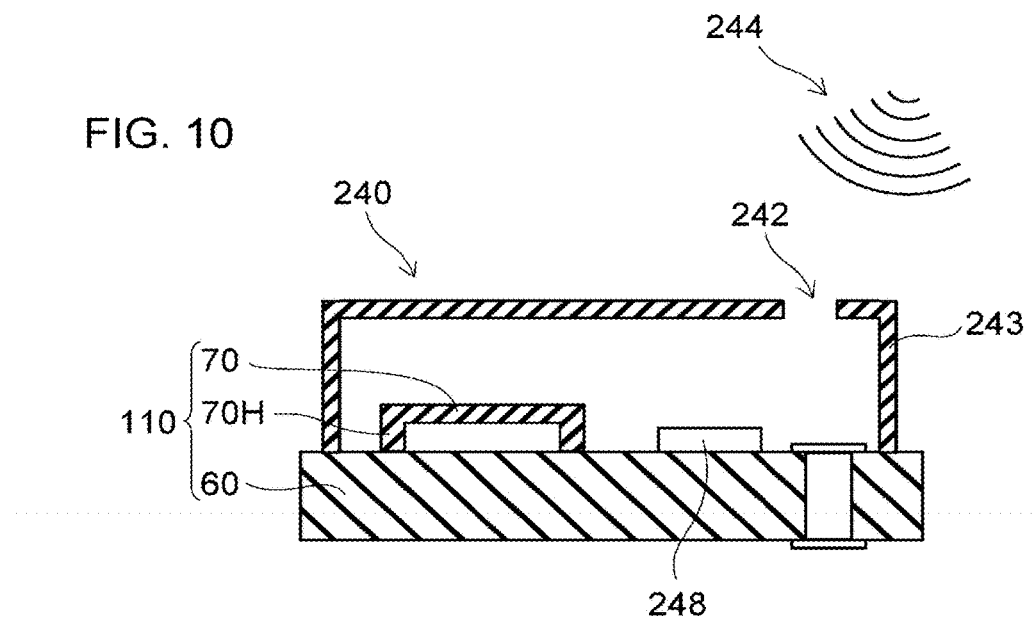
FIG. 10 is a schematic cross-sectional view which illustrates a microphone or an ultrasonic sensor according to a fourth embodiment.

FIG. 10 is a schematic cross-sectional view which illustrates a microphone or an ultrasonic sensor according to a fourth embodiment. As illustrated in FIG. 10, the microphone 240 according to the embodiment includes the pressure sensor 110 according to the first embodiment described above.

On a substrate 60 of the pressure sensor 110, circuits 248 such as amplifiers are provided. A cover 243 in which an opening 242 is formed is provided to cover a membrane part 70 through a space. A sound wave 244 enters the inside of the cover 243 through the opening 242. The microphone 240 responds to sound pressure of the sound wave 244. The sound wave 244 is a signal of an audible range, but the sound wave may include an ultrasonic wave.

Figure 11:
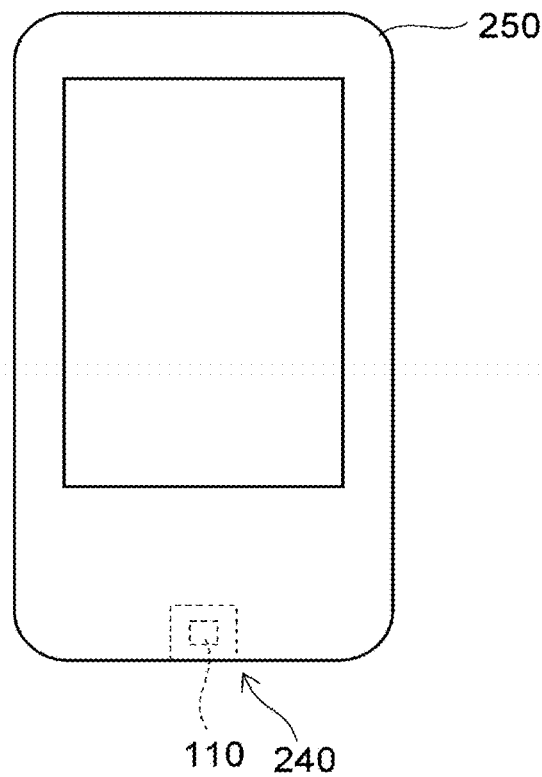
FIG. 11 is a schematic diagram which illustrates a used state of the microphone.

FIG. 11 is a schematic diagram which illustrates a used state of the microphone according to the fourth embodiment as an example. As illustrated in FIG. 11, the microphone 240 including the pressure sensor 110 illustrated in FIG. 10 may be built in a mobile information terminal 250. The microphone 240 may be used for an IC recorder, a pin microphone, or the like.

Figure 12:
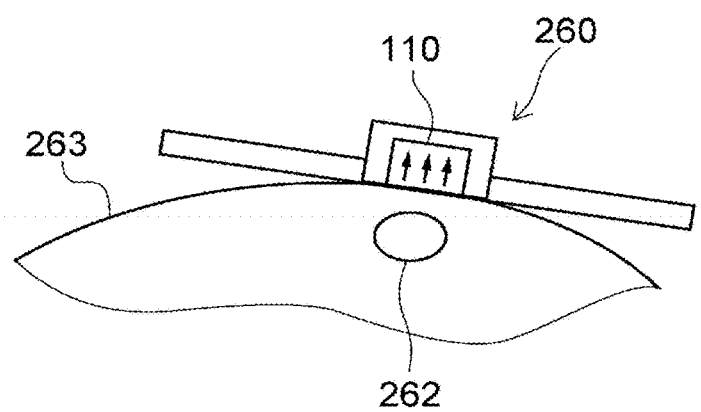
FIG. 12 is a schematic diagram which illustrates a blood pressure sensor according to a fifth embodiment.

FIG. 12 is a schematic diagram which illustrates a blood pressure sensor according to a fifth embodiment. As illustrated in FIG. 12, the blood pressure sensor 260 includes the pressure sensor 110 according to the first embodiment. The blood pressure sensor 260 is used for measuring person's blood pressure, and continuously measures blood pressure by pressing the pressure sensor 110 to a skin 263 provided on an arterial vessel 262, for example. According to the embodiment, the pressure sensor capable of enhancing the sensitivity can be provided.

Figure 13:
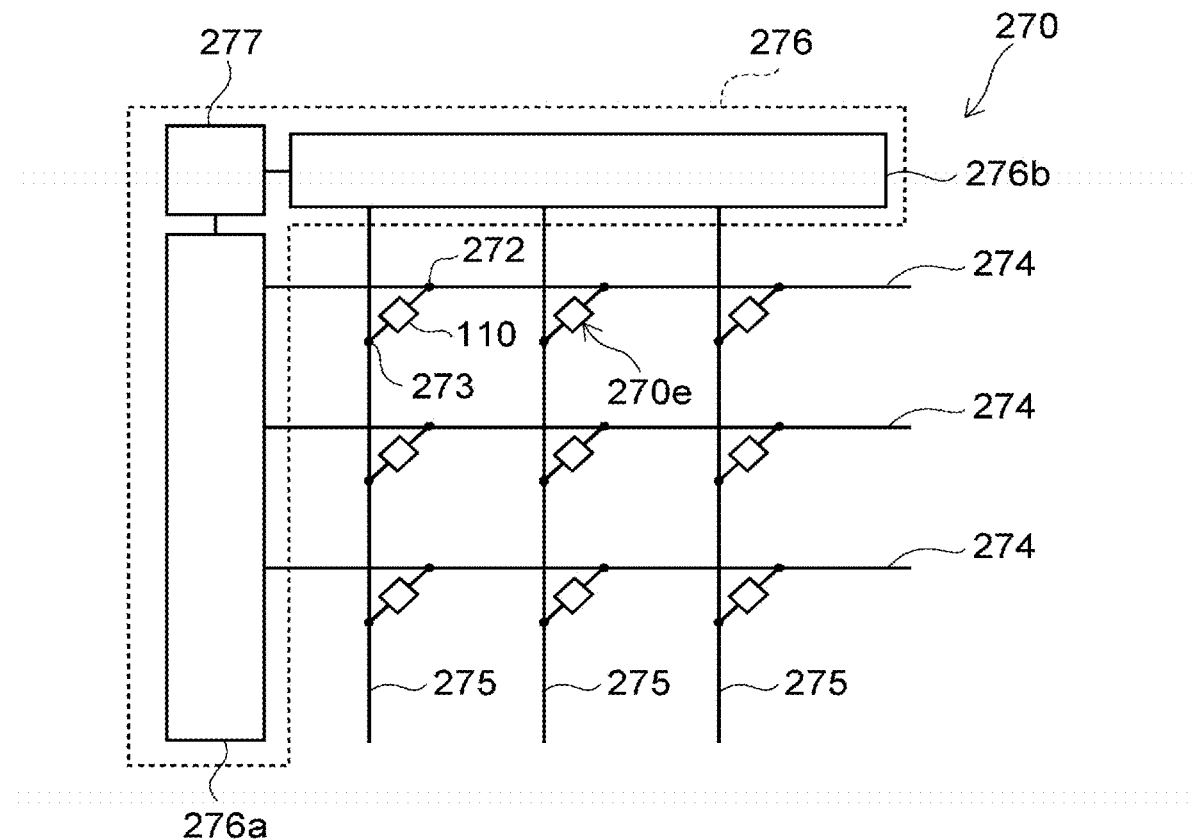
FIG. 13 is a schematic diagram which illustrates a touch panel according to a sixth embodiment.

FIG. 13 is a schematic diagram which illustrates a touch panel according to a sixth embodiment. As illustrated in FIG. 13, the touch panel 270 according to the embodiment includes a plurality of the pressure sensors 110 according to the first embodiment. In addition, the touch panel 270 includes a plurality of first wirings 274, a plurality of second wirings 275, and a control portion 276. The pressure sensors 110, for example, are mounted in at least one of the inside and the outside of a display device.

The first wirings 274 extend in one direction spaced-apart from each other. The second wirings 275 extend in a direction so as to intersect the above-described direction and spaced-apart from each other.

The pressure sensors 110 are provided at intersecting portions of the first wirings 274 and the second wirings 275. Each of the pressure sensor 110 serves as a detecting element 270e which is used to detect pressure. Each of the intersecting portions includes a position at which a first wiring 274 and a second wiring 275 intersect with each other and the peripheral area of the position.

One end 272 of each of the pressure sensors 110 is connected to one of the first wirings 274. The other end 273 of each of the pressure sensors 110 is connected to one of the second wirings 275.

The control portion 276 is connected to the first wirings 274 and the second wirings 275. The control portion 276 includes a first circuit 276a, connected to the first wirings 274 and a second circuit 276b connected to the second wirings 275. The touch panel 270 includes a control circuit 277 which is connected to the first circuit 276a and the second circuit 276b.

By using the pressure sensors 110 of the first embodiment in the above manner, pressure sensitivity can be high and the size of the touch panel 270 is small, and a high definition touch panel can be realized.

The pressure sensors according of the first to third embodiments described above and the pressure sensors of the plurality of the modified examples of the embodiments can be used for a gas pressure sensor or a pneumatic sensor.

The above-described "vertical" and "parallel" represent not only "vertical" and "parallel" in a strict meaning but also those including variation in a manufacturing process etc. The "vertical" and "parallel" may be substantially vertical and substantially parallel.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A pressure sensor comprising:
a support portion;
a transformable membrane part which includes a first end portion supported by the support portion, a first area positioned between a center of the membrane part and the first end portion and having a first rigidity, and a second area positioned between the first area and the first end portion where a sensor portion is not provided and having a second rigidity lower than the first rigidity; and
a first sensor portion which is provided at the first area and includes a first magnetic layer, a second magnetic layer, and a first intermediate layer provided between the first magnetic layer and the second magnetic layer,
wherein a first end-side distance between the first area and the first end portion is shorter than a first center-side distance between the second area and the center of the membrane part where the first sensor portion is provided, and a sensor portion other than the first sensor portion is not provided at the second area.

2. The pressure sensor according to claim 1, wherein a thickness of the second area is thinner than a thickness of the first area.

3. The pressure sensor according to claim 1, wherein a Young's modulus of the second area is lower than a Young's modulus of the first area.

4. The pressure sensor according to claim 1, wherein the second area has a corrugated shape.

5. The pressure sensor according to claim 1,
wherein a first length of the membrane part along a first in-plane direction which is perpendicular to a stacking direction from the first area toward the first sensor portion is shorter than a second length of the membrane part along a second in-plane direction which is perpendicular to the stacking direction and the first in-plane direction,
the membrane part includes a first side along the first in-plane direction and a second side along the second in-plane direction, and
the second area extends along the first side and the second side.

6. A microphone comprising the pressure sensor according to claim 1.

7. An ultrasonic sensor comprising the pressure sensor according to claim 1.

8. A blood pressure sensor comprising the pressure sensor according to claim 1.

9. A touch panel comprising the pressure sensor according to claim 1.

10. A pressure sensor comprising:
a support portion;
a membrane part which has flexibility and includes a first end portion supported by the support portion, a first area positioned between a center of the membrane part and the first end portion, and a second area positioned between the first area and the first end portion where a sensor portion is not provided; and
a first sensor portion which is provided at the first area and includes a first magnetic layer, a second magnetic layer and a first intermediate layer provided between the first magnetic layer and the second magnetic layer,
wherein the second area includes a first portion which extends in a first direction from the center toward the first end portion and a second portion which is connected to the first portion and extends in a second direction from the first area toward the first sensor portion, and
a first end-side distance between the first area and the first end portion is shorter than a first center-side distance between the second area and the center of the membrane part.

11. The pressure sensor according to claim 10, wherein a plurality of first portions including the first portion and extending in the first direction are provided in the second area, and the second portion is provided between the first portions.

12. The pressure sensor according to claim 10, wherein a plurality of first portions including the first portion and extending in the first direction and a plurality of second portions including the second portion and extending in the second direction are provided in the second area, and the first portions and the second portions are alternately arranged.

13. The pressure sensor according to claim 12, wherein the second area has a corrugated shape configured by the first portions and the second portions.

14. The pressure sensor according to claim 10, wherein a planar shape of the membrane part is one of a rectangle, a square, a polygon, a circle, or an elongated circle.

15. The pressure sensor according to claim 10, wherein a plurality of first sensor portions including the first sensor portion are provided in the first area, and at least two of the first sensor portions are aligned in a direction intersecting the first direction.

16. The pressure sensor according to claim 10,
wherein a first length of the membrane part along a first in-plane direction which is perpendicular to a stacking direction from the first area toward the first sensor portion is shorter than a second length of the membrane part along a second in-plane direction which is perpendicular to the stacking direction and the first in-plane direction,
the membrane part includes a first side along the first in-plane direction and a second side along the second in-plane direction, and
the second area extends along the first side and the second side.

17. A microphone comprising the pressure sensor according to claim 10.

18. An ultrasonic sensor comprising the pressure sensor according claim 10.

19. A blood pressure sensor comprising the pressure sensor according to claim 10.

20. A touch panel comprising the pressure sensor according to claim 10.

* * * * *